United States Patent [19]

Furutaka et al.

[11] Patent Number: 5,171,899
[45] Date of Patent: Dec. 15, 1992

[54] PROCESS FOR PRODUCTION OF 1,1,1-TRIFLUORO-2,2-DICHLOROETHANE

[75] Inventors: Yasuhisa Furutaka, Takatsuki; Yukio Homoto, Katano; Tsunetoshi Honda, Settsu, all of Japan

[73] Assignee: Daikin Industries Ltd., Osaka, Japan

[21] Appl. No.: 586,372

[22] Filed: Sep. 21, 1990

Related U.S. Application Data

[63] Continuation of Ser. No. 349,176, May 9, 1989, abandoned.

[30] Foreign Application Priority Data

May 17, 1988 [JP] Japan ................................ 63-120067

[51] Int. Cl.$^5$ .................... C07C 17/10; C07C 19/02
[52] U.S. Cl. .................... 570/123; 570/134; 570/164
[58] Field of Search ........................ 570/123

[56] References Cited

U.S. PATENT DOCUMENTS

| | | | |
|---|---|---|---|
| 2,644,845 | 7/1955 | McBee | 570/123 |
| 3,715,378 | 2/1973 | Sianesi et al. | 260/463 |
| 3,755,477 | 8/1973 | Firth et al. | 260/653.4 |
| 4,046,823 | 9/1977 | Gorden et al. | 570/254 |
| 4,060,469 | 11/1977 | Sweeney et al. | 204/163 R |
| 4,145,368 | 3/1979 | Sweeney et al. | 570/123 |
| 4,528,174 | 7/1985 | Schmidhammer et al. | 570/254 |

FOREIGN PATENT DOCUMENTS

| | | |
|---|---|---|
| 0180996 | 5/1986 | European Pat. Off. . |
| 0244838 | 11/1987 | European Pat. Off. . |
| 53-82711 | 7/1978 | Japan . |
| 58-222038 | 12/1983 | Japan . |
| 61-27375 | 6/1986 | Japan . |
| A81460 | 10/1979 | Luxembourg . |
| WO88/00963 | 2/1988 | PCT Int'l Appl. . |

OTHER PUBLICATIONS

McBee et al., "Fluorinated Derivatives of Ethane," Industrial & Engineering Chemistry, Mar. 1947, vol. 39, No. 3, pp. 409-412.

Primary Examiner—Joseph E. Evans
Attorney, Agent, or Firm—Birch, Stewart, Kolasch & Birch

[57] ABSTRACT

A process for production of 1,1,1-trifluoro-2,2-dichloroethane comprising chlorinationo f 1,1,1-trifluoro-2-chloroethane with chlorine gas in the presence or absence of a metal salt as a catalyst.

3 Claims, No Drawings

PROCESS FOR PRODUCTION OF 1,1,1-TRIFLUORO-2,2-DICHLOROETHANE

This application is a continuation of application Ser. No. 07/349,176 filed on May 9, 1989, now abandoned.

BACKGROUND OF THE INVENTION

1. Field of the Invention

The present invention relates to a process for the production of 1,1,1-trifluoro-2,2-dichloroethane. Particularly, the present invention relates to a process for the production of 1,1,1-trifluoro-2,2-dichloroethane comprising chlorination of 1,1,1-trifluoro-2-chloroethane with chlorine gas in the presence or absence of a metal salt as a catalyst.

2. Description of the Related Art 1,1,1-Trifluoro-2,2-dichloroethane is expected to replace trichlorofluoromethane, since it does not decompose ozone in the stratosphere. Thus, it is desirable to develop an economical process for the production of 1,1,1-trifluoro-2,2-dichloroethane.

Several processes for the production of 1,1,1-trifluoro-2,2-dichloroethane have been already proposed. For example, Czechoslovakian Patent No. 136,735 and Japanese Patent Kokai Publication No. 222038/1983 describe a process comprising reduction of 1,1,1-trifluoro-2,2,2-trichloroethane. Japanese Patent Publication No. 27375/1986 describes a process comprising isomerization of 1,1,2-trifluoro-1,2-dichloroethane. U.S. Pat. No. 3,755,477 describes a process comprising fluorination of ethylene tetrachloride. Japanese Patent Kokai Publication No. 82711/1978 describes a process comprising photo chlorination of 1,1,1-trifluoro-2-chloroethane. McBee describes a process comprising chlorination of 1,1,1-trifluoroethane in J. Ind. Eng. Chem., 39, 409, (1947).

However, from a point of view of the economical production, the above known processes for the production of 1,1,1.trifluoro-2,2-dichloroethane are not necessarily suitable since the yield and selectivity through such processes are not sufficiently high.

McBee describes that 1,1,1-trifluoroethane, which is a compound which is similar to a starting material for the production of 1,1,1-trifluoro-2,2-dichloroethane, reacts at a reaction temperature of 485° C. with chlorine at a molar ratio of 1:1. Under these conditions, the conversion of 1,1,1-trifluoroethane is 50%. The product produced by this process contains 22.5% of 1,1,1-trifluoro-2,2-dichloroethane and 41.8% of 1,1,1-trifluoro-2,2,2-trichloroethane. It has been reported that, judging from the fact that the amounts of the compounds of which all hydrogen atoms are replaced with chlorine atoms have been increased, the chlorination rate increases, as the chlorination proceeds, or as the number of hydrogen atoms replaced with chlorine atoms increases.

Accordingly, the above report indicates that the molar ratio of 1,1,1-trifluoro-2,2,2-trichloroethane to 1,1,1-trifluoro-2,2-dichloroethane is more than 1, that is, the amount of 1,1,1-trifluoro-2,2,2-trichloroethane produced is always more than 1,1,1-trifluoro-2,2-dichloroethane.

SUMMARY OF THE INVENTION

It is, therefore, an object of the present invention to provide a commercially advantageous process for the production of 1,1,1-trifluoro-2,2-dichloroethane in which the problems described above are overcome.

According to the present invention, there is provided a process for the production of 1,1,1-trifluoro-2,2-dichloroethane which process comprises chlorination of 1,1,1-trifluoro-2-chloroethane with chlorine gas in the presence or absence of a metal salt as a catalyst.

In the process of the present invention, the production ratio of 1,1,1-trifluoro-2,2-dichloroethane to 1,1,1-trifluoro-2,2,2-trichloroethane is about 1:0.3 at about 50% conversion of 1,1,1-trifluoro-2-chloroethane and such the high production ratio cannot be expected from the report of McBee. Accordingly, it becomes possible to produce 1,1,1-trifluoro-2,2-dichloroethane economically.

DETAILED DESCRIPTION OF THE INVENTION 1,1,1-Trifluoro-2-chloroethane, as a starting material in the present process, can be easily produced by fluorination of trichloroethylene with anhydrous hydrogen fluoride in a liquid or gas phase.

The chlorination of the present invention can proceed with high selectivity even in the absence of a catalyst. Further, when a metal salt is used as the catalyst, higher selectivity can be achieved.

such a metal salt optionally used in the present process includes a metal fluoride such as $CrF_3$ and a metal chloride such as $CuCl_2$, $NiCl_2$ and $FeCl_2$.

It is preferable to use a metal salt which is carried on, for example, a support made of a metal oxide such as aluminum oxide or activated carbon. The most preferable catalyst includes $NiCl_2$, $CuCl_2$ and $FeCl_2$ carried on a support made of aluminum fluoride. Further, the support itself can be used as a catalyst, that is the support above can be used, without the catalytic compound describe above, which also provides good production.

Generally, any type of support can be used, and it is most preferable to use a spherical support or a pellet form support of a size within the range of from 1 to 8 mm, particularly from 2 to 4 mm.

The amount of catalyst carried on the support is suitably selected depending on the reaction conditions, the desired conversion and so on. Generally, the molar ratio of the metal salt as the catalyst to the metal oxide as the support, is in the range of from 0.005 to 2, preferably from 0.01 to 1.0, for example, 0.03.

The reaction temperature of the chlorination of the present process is generally in the range of from 250° to 500° C., preferably from 350° to 450° C., for example 400° C. The reaction is usually performed under atmospheric pressure, although the present chlorination can be performed under pressure.

The molar ratio of chlorine gas to 1,1,1-trifluoro-2-chloroethane is preferably controlled in the range of from 0.05 to 0.5, particularly from 0.1 to 0.4 by taking into account the selectivity to 1,1,1-trifluoro-2,2-dichloroethane.

The contact time between the catalyst and the reactants can be suitably selected depending on the reaction conditions, especially the reaction temperature. Generally, the contact time is preferably controlled in the range of from 0.5 to 30 seconds, particularly from 1 to 25 seconds.

In the present process, any type of reactor, for example a tube reactor, can be used as long as good contact between the catalyst and the reactants can be ensured.

In the process of the present invention, the reactor such as a tube reactor filled with the support carrying a catalyst is heated to a preselected temperature dependent on the reaction temperature, for example, in an electrical furnace. Then, 1,1,1-trifluoro-2-chloroethane and chlorine gas are supplied to the reactor to initiate the chlorination. The exit gas from the reactor is generally collected after water washing and drying steps.

In order to improve the conversion of 1,1,1-trifluoro-2-chloroethane, it is advantageous to recycle the unreacted 1,1,1-trifluoro-2-chloroethane to the reactor which is recovered from the top of a purification apparatus for purifying the produced gas.

When no catalyst is used in the present process, it is advantageous to use an inert packing such as Raschig ring from the view point achieving better mixing of the gas and better heat transfer.

The present invention will be hereinafter explained further in detail by following examples.

EXAMPLE 1

A tube reactor made of Hastelloy C (20 mm in inner diameter, 400 mm in length) was filled with 50 ml of spherical support particles (from 2 to 4 mm in diameter) made of $AlF_3$ carrying $CuCl_2$ in the molar ratio of 0.03 to $AlF_3$, and then heated to 370° C. in a nitrogen stream. After stopping the supply of nitrogen, 1,1,1-trifluoro-2-chloroethane and chlorine gas were supplied to the reactor at the flow rate of 100 ml/min. and 50 ml/min. (based on the standard conditions), respectively. The contact time based on the average residence time was about 8.5 seconds.

The exit gas from the tube reactor was collected after the water washing and the drying steps, and then analyzed with a gas chromatography. The conversion of 1,1,1-trifluoro-2-chloroethane was 45% and the selectivity to 1,1,1trifluoro-2,2-dichloroethane was 75%.

EXAMPLES 2-4

Using the same apparatus as Example 1, the process of the present invention was carried out without a catalyst. In these examples, 1,1,1-trifluoro-2-chloroethane was reacted with chlorine gas at the temperature of 400° C. with the ratio of the flow rate thereof as shown in Table 1. The exit gas from the reactor was analyzed as in Example 1.

The results are also shown in Table 1.

TABLE 1

|  | Example 2 | Example 3 | Example 4 |
|---|---|---|---|
| Flow rate of 1,1,1-trifluoro-2-chloroethane | 90 ml/min. | 80 ml/min. | 70 ml/min. |
| Flow rate of chlorine gas | 10 ml/min. | 20 ml/min. | 30 ml/min. |
| Conversion of 1,1,1-trifluoro-2-chloroethane | 10% | 22% | 40% |
| Selectivity to 1,1,1-trifluoro-2,2-dichloroethane | 91% | 86% | 77% |

TABLE 1-continued

|  | Example 2 | Example 3 | Example 4 |
|---|---|---|---|
| 2,2-dichloroethane |  |  |  |

EXAMPLES 5-9

Example 1 was repeated except that the metal salt shown in Table 2 carried on the $AlF_3$ support particles in the molar ratio of 0.03 was used and the reaction temperature was changed as shown in Table 2.

The results are also shown in Table 2.

TABLE 2

|  | Example 5 | Example 6 | Example 7 | Example 8 | Example 9 |
|---|---|---|---|---|---|
| Catalyst | $FeCl_2/AlF_3$ | $FeCl_2/AlF_3$ | $NiCl_2/AlF_3$ | $NiCl_2/AlF_3$ | $AlF_3$ |
| Reaction temperature | 330° C. | 370° C. | 330° C. | 370° C. | 450° C. |
| Conversion of 1,1,1-trifluoro-2-chloroethane | 32% | 48% | 26% | 51% | 79% |
| Selectivity to 1,1,1-trifluoro-2,2-dichloroethane | 82% | 72% | 83% | 71% | 45% |

COMPARATIVE EXAMPLE 1,1,1-Trifluoro-2-chloroethane and chlorine gas were supplied to a glass tube reactor (30 mm in inner diameter, 200 mm in length) made of Pyrex Glass ® (commercially available from Corning Glass Works, U.S.) under the illumination of a high pressure mercury lamp of 100 wattages. Their flow rates were 100 ml/min. and 50 ml/min., respectively. The residence time in the reactor was about 60 seconds. The temperature in the reactor was 30° C.

The produced gas discharged from the reactor was analyzed with the gas chromatography after water washing. The conversion of 1,1,1-trifluoro-2-chloroethane was 5% and the selectivity to 1,1,1-trifluoro-2,2-dichloroethane was 10%. The remainder of the product was 1,1,1-trifluoro-2,2,2-trichloroethane.

What is claimed is:

1. A process for production of 1,1,1-trifluoro-2,2-dichloroethane comprising chlorination of 1,1,1-trifluoro-2-chloroethane with chlorine gas in the presence of a metal salt catalyst selected from aluminum fluoride or $CfF_3$, in which a molar ratio of chlorine gas to 1,1,1-trifluoro-2-chloroethane is in the range of from 0.05 to 0.5.

2. The process according to claim 1, wherein the metal salt is aluminum fluoride.

3. The process according to claim 1, wherein the metal salt is $CrF_3$.

* * * * *

UNITED STATES PATENT AND TRADEMARK OFFICE
CERTIFICATE OF CORRECTION

PATENT NO. : 5,171,899
DATED : December 15, 1992
INVENTOR(S) : Furutaka et al.

It is certified that error appears in the above-indentified patent and that said Letters Patent is hereby corrected as shown below:

IN THE ABSTRACT:

Line 2, change "chlorinationo f" to --chlorination of--.

Column 4, line 52:

Claim 1, line 5, delete "$CfF_3$," and insert --$CrF_3$--.

Signed and Sealed this

Twenty-seventh Day of September, 1994

Attest:

BRUCE LEHMAN

Attesting Officer

Commissioner of Patents and Trademarks